US010078265B2

(12) United States Patent
Aoki et al.

(10) Patent No.: US 10,078,265 B2
(45) Date of Patent: Sep. 18, 2018

(54) PATTERN-FORMING METHOD, RESIN, AND COMPOSITION

(71) Applicant: JSR CORPORATION, Tokyo (JP)

(72) Inventors: Shun Aoki, Tokyo (JP); Hiromitsu Tanaka, Tokyo (JP); Goji Wakamatsu, Tokyo (JP); Yoshio Takimoto, Tokyo (JP); Masayoshi Ishikawa, Tokyo (JP); Toru Kimura, Tokyo (JP)

(73) Assignee: JSR CORPORATION, Tokyo (JP)

( * ) Notice: Subject to any disclaimer, the term of this patent is extended or adjusted under 35 U.S.C. 154(b) by 0 days.

(21) Appl. No.: 15/267,923

(22) Filed: Sep. 16, 2016

(65) Prior Publication Data
US 2017/0003595 A1 Jan. 5, 2017

Related U.S. Application Data

(63) Continuation of application No. PCT/JP2015/056424, filed on Mar. 4, 2015.

(30) Foreign Application Priority Data

Mar. 24, 2014 (JP) .................... 2014-060960

(51) Int. Cl.
G03F 7/11 (2006.01)
G03F 7/09 (2006.01)
G03F 7/38 (2006.01)
G03F 7/075 (2006.01)
G03F 7/32 (2006.01)
C07C 279/08 (2006.01)
H01L 21/308 (2006.01)
H01L 21/027 (2006.01)
H01L 21/02 (2006.01)
C07C 217/18 (2006.01)
H01L 21/306 (2006.01)
C08L 61/06 (2006.01)
C08G 8/04 (2006.01)
G03F 7/26 (2006.01)
C08G 8/20 (2006.01)
C08G 8/36 (2006.01)
C09D 161/14 (2006.01)
C09D 183/04 (2006.01)
G03F 7/40 (2006.01)

(52) U.S. Cl.
CPC ............ G03F 7/11 (2013.01); C07C 217/18 (2013.01); C07C 279/08 (2013.01); C08G 8/04 (2013.01); C08G 8/20 (2013.01); C08G 8/36 (2013.01); C08L 61/06 (2013.01); C09D 161/14 (2013.01); C09D 183/04 (2013.01); G03F 7/075 (2013.01); G03F 7/094 (2013.01); G03F 7/26 (2013.01); G03F 7/322 (2013.01); G03F 7/38 (2013.01); G03F 7/405 (2013.01); H01L 21/02057 (2013.01); H01L 21/0274 (2013.01); H01L 21/3081 (2013.01); H01L 21/30604 (2013.01); Y02P 20/582 (2015.11)

(58) Field of Classification Search
CPC ... G03F 7/11; G03F 7/094; G03F 7/26; G03F 7/075; G03F 7/322; G03F 7/38; C07C 217/18; C07C 279/08; H01L 21/0274; H01L 21/02057; H01L 21/3081; H01L 21/30604; C08L 61/06; C08G 8/04; C08G 8/20
USPC ......... 430/271.1, 272.1, 322, 325, 329, 330, 430/331; 568/632, 631
See application file for complete search history.

(56) References Cited

U.S. PATENT DOCUMENTS

| 6,045,968 | A | * | 4/2000 | Ushirogouchi | ....... | G03F 7/0045 430/270.1 |
| 8,088,554 | B2 | * | 1/2012 | Hatakeyama | ............ | G03F 7/094 430/270.1 |
| 8,465,902 | B2 | * | 6/2013 | Yao | ....................... | C09D 161/24 430/270.1 |
| 8,592,134 | B2 | * | 11/2013 | Oguro | ..................... | C08G 10/02 430/270.1 |
| 8,663,898 | B2 | * | 3/2014 | Ogihara | .................. | G03F 7/091 430/270.1 |

(Continued)

FOREIGN PATENT DOCUMENTS

CN 102241181 A 11/2011
JP 06242607 A * 9/1994

(Continued)

OTHER PUBLICATIONS

Machine translation of JP 06-242607 (no date).*

(Continued)

Primary Examiner — Amanda C Walke
(74) Attorney, Agent, or Firm — Oblon, McClelland, Maier & Neustadt, L.L.P.

(57) ABSTRACT

A pattern-forming method comprises: forming a resist underlayer film on an upper face side of a substrate; forming a silicon-containing film on an upper face side of the resist underlayer film; and removing at least a part of the resist underlayer film and at least a part of the silicon-containing film with a basic aqueous solution. Preferably, the pattern-forming method further comprises, after the forming of the silicon-containing film and before the removing of the resist underlayer film and the silicon-containing film, forming a resist pattern on an upper face side of the silicon-containing film, and etching the silicon-containing film using the resist pattern as a mask.

20 Claims, No Drawings

(56) References Cited

U.S. PATENT DOCUMENTS

| | | | |
|---|---|---|---|
| 9,005,873 B2* | 4/2015 | Sakamoto | G03F 7/091 |
| | | | 430/270.1 |
| 9,207,535 B2* | 12/2015 | Ogihara | C09D 183/06 |
| 9,244,353 B2* | 1/2016 | Nishimaki | C08G 8/04 |
| 9,263,285 B2* | 2/2016 | Shinjo | C09D 139/04 |
| 9,400,429 B2* | 7/2016 | Toyokawa | G03F 7/26 |
| 2007/0042292 A1* | 2/2007 | Yoneda | G03F 7/0045 |
| | | | 430/270.1 |
| 2010/0131392 A1* | 5/2010 | Archer | G06Q 30/02 |
| | | | 705/26.1 |

FOREIGN PATENT DOCUMENTS

| | | | |
|---|---|---|---|
| JP | 10120628 A * | 5/1998 | |
| JP | 2004-168748 A | 6/2004 | |
| JP | 2004-177668 A | 6/2004 | |
| JP | 2006-208658 A | 8/2006 | |
| JP | 2009-175465 A | 8/2009 | |
| JP | 2009-241300 A | 10/2009 | |
| JP | 2010-085912 A | 4/2010 | |
| JP | 2010-515107 A | 5/2010 | |
| JP | 2010-139764 A | 6/2010 | |
| JP | 2011-219752 A | 11/2011 | |
| JP | 2012-192724 A | 10/2012 | |
| TW | 200827936 A | 7/2008 | |
| WO | WO 2008/081416 A2 | 7/2008 | |
| WO | WO 2014/038680 A1 | 3/2014 | |

OTHER PUBLICATIONS

International Search Report dated Jun. 2, 2015, in PCT/JP2015/056424 filed Mar. 4, 2015 (w/ English translation).

Office Action dated Jun. 5, 2018 in Japanese Patent Application No. 2016-510192 (w/ Computer-generated English translation).

Office Action dated Jul. 17, 2018 in Taiwan Patent Application No. 104109183 citing AO and AP (w/ English translation).

* cited by examiner

PATTERN-FORMING METHOD, RESIN, AND COMPOSITION

CROSS-REFERENCE TO RELATED APPLICATIONS

The present application is a continuation application of International Application No. PCT/JP2015/056424, filed Mar. 4, 2015, which claims priority to Japanese Patent Application No. 2014-060960, filed Mar. 24, 2014. The contents of these applications are incorporated herein by reference in their entirety.

BACKGROUND OF THE INVENTION

Field of the Invention

The present invention relates to a pattern-forming method, a resin, and a composition.

Discussion of the Background

In the field of manufacture of semiconductors and the like, a reduction in pattern size has progressed by utilizing a multilayer resist process in order to achieve a higher degree of integration. As the multilayer resist process, a three-layer resist process in which a silicon-containing film is formed between an organic resist underlayer film (hereinafter, may be also merely referred to as "resist underlayer film") and a resist film is known.

In an actual manufacture process of the semiconductor and the like, in a case where defects are generated in patterning of the resist film, the silicon-containing film and the resist underlayer film, refabrication may be carried out. In regard to the refabrication, in order to remove the silicon-containing film, a wet removal method in which a treatment with an alkaline removing liquid is carried out after a step of a treatment with an acidic removing liquid containing a sulfate ion and/or a fluorine ion (see Japanese Unexamined Patent Application, Publication No. 2010-139764), wet removal that involves the use of a wet removal composition containing a fluoride source and an ammonium salt (see Japanese Unexamined Patent Application (Translation of PCT Application), Publication No. 2010-515107) or the use of concentrated aqueous hydrogen fluoride, as well as dry removal (see Japanese Unexamined Patent Application, Publication No. 2010-85912), and the like have been proposed.

Japanese Unexamined Patent Application, Publication No. 2004-177668 proposes removal of an underlayer resist pattern composed of an organic material with a resist removing liquid containing a water soluble amine or quaternary ammonium hydroxide after removal of an intermediate layer resist pattern composed of a spin-on-glass material. However, Japanese Unexamined Patent Application, Publication No. 2004-177668 does not disclose removal of the intermediate layer resist pattern with the resist removing liquid.

SUMMARY OF THE INVENTION

According to an aspect of the present invention, a pattern-forming method comprises: forming a resist underlayer film on an upper face side of a substrate; forming a silicon-containing film on an upper face side of the resist underlayer film; forming a resist pattern on an upper face side of the silicon-containing film; etching the silicon-containing film using the resist pattern as a mask; and removing at least a part of the resist underlayer film and at least a part of the silicon-containing film with a basic aqueous solution.

According to another aspect of the present invention, a resin comprises a structural unit represented by formula (1-1).

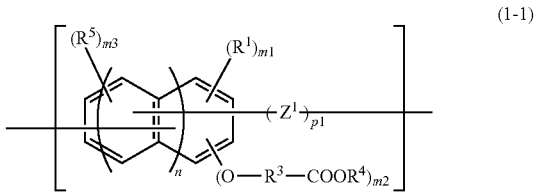

In the formula (1-1), $Z^1$ represents a substituted or unsubstituted alkanediyl group, a substituted or unsubstituted arenediyl group or a substituted or unsubstituted oxyalkanediyl group; p1 represents number of $Z^1$ that bonds to the aromatic ring, and is an integer of 1 to 10, wherein in a case where p1 is no less than 2, a plurality of $Z^1$s are identical or different; $R^1$ and $R^5$ each independently represent a monovalent organic group having 1 to 20 carbon atoms; m1 is an integer of 0 to 6, wherein in a case where m1 is no less than 2, a plurality of $R^1$s are identical or different; m3 is an integer of 0 to 6, wherein in a case where m3 is no less than 2, a plurality of $R^5$s are identical or different; m2 is an integer of 1 to 8; $R^3$ represents a divalent organic group having 1 to 20 carbon atoms; $R^4$ represents a tertiary alkyl group, wherein in a case where m2 is no less than 2, a plurality of $R^3$s are identical or different and a plurality of $R^4$s are identical or different; and n is an integer of 0 to 2. A sum of m1, m2, m3 and p1 is no greater than 10.

According to further aspect of the present invention, a composition comprises a solvent and a resin which comprises a structural unit represented by formula (1-1):

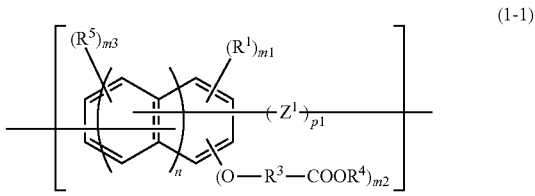

In the formula (1-1), $Z^1$ represents a substituted or unsubstituted alkanediyl group, a substituted or unsubstituted arenediyl group or a substituted or unsubstituted oxyalkanediyl group; p1 represents number of $Z^1$ that bonds to the aromatic ring, and is an integer of 1 to 10, wherein in a case where p1 is no less than 2, a plurality of $Z^1$s are identical or different; $R^1$ and $R^5$ each independently represent a monovalent organic group having 1 to 20 carbon atoms; m1 is an integer of 0 to 6, wherein in a case where m1 is no less than 2, a plurality of $R^1$s are identical or different; m3 is an integer of 0 to 6, wherein in a case where m3 is no less than 2, a plurality of $R^5$s are identical or different; m2 is an integer of 1 to 8; $R^3$ represents a divalent organic group having 1 to 20 carbon atoms; $R^4$ represents a tertiary alkyl group, wherein in a case where m2 is no less than 2, a plurality of $R^3$s are identical or different and a plurality of $R^4$s are identical or different; and n is an integer of 0 to 2. A sum of m1, m2, m3 and p1 is no greater than 10.

DESCRIPTION OF THE EMBODIMENTS

According to an embodiment of the present invention, a pattern-forming method includes: the step of forming a resist underlayer film on an upper face side of a substrate (hereinafter, may be also referred to as "resist underlayer film-forming step"); the step of forming a silicon-containing film on an upper face side of the resist underlayer film (hereinafter, may be also referred to as "silicon-containing film-forming step"); the step of forming a resist pattern on the silicon-containing film (hereinafter, may be also referred to as "resist pattern-forming step"); the step of etching the silicon-containing film using the resist pattern as a mask (hereinafter, may be also referred to as "etching step"); and the step of removing at least a part of the resist underlayer film and at least a part of the silicon-containing film with a basic aqueous solution (hereinafter, may be also referred to as "resist underlayer film and silicon-containing film-removing step").

According to the pattern-forming method of the embodiment of the present invention, the resist underlayer film and the silicon-containing film can be removed by dissolving the resist underlayer film without causing a severe damage to the substrate and reprocessing of the substrate is enabled. In addition, the resist underlayer film and the like can be conveniently removed without utilizing an ashing treatment and the like after the formation of the pattern of the substrate, and therefore an influence etc. of the ashing treatment and the like on the substrate can be minimized. Therefore, the pattern-forming method can be suitably used for manufacture of semiconductor devices in which further progress of miniaturization is expected in the future. Hereinafter, the embodiments of the present invention will be described in detail.

Pattern-Forming Method

A pattern-forming method according to an embodiment of the present invention includes the resist underlayer film-forming step, the silicon-containing film-forming step, and the resist underlayer film and silicon-containing film-removing step. Typically, the pattern-forming method includes the resist pattern-forming step and the etching step after the silicon-containing film-forming step and before the resist underlayer film and silicon-containing film-removing step.

The time period during which the resist underlayer film and silicon-containing film-removing step may be carried out is exemplified by the following (i) to (iv). First, the resist underlayer film and silicon-containing film-removing step may be carried out (i) after the resist pattern-forming step. In this case, the resist film not patterned properly can be removed together with the resist underlayer film and the silicon-containing film by dissolving the resist underlayer film, whereby refabrication which may include e.g., re-formation of the resist underlayer film, the silicon-containing film and the resist film on the substrate through reusing the substrate, and the like is enabled. Alternatively, the resist underlayer film and silicon-containing film-removing step may also be carried out (ii) after further etching the silicon-containing film in the etching step. In this case, since the silicon-containing film not patterned properly and the like can be removed together with the resist underlayer film in the resist underlayer film and silicon-containing film-removing step, whereby refabrication which may include e.g., re-formation of the resist underlayer film, the silicon-containing film and the like on the substrate through reusing the substrate, and the like is enabled. Further, the resist underlayer film and silicon-containing film-removing step may also be carried out (iii) after further etching the resist underlayer film in the etching step. Furthermore, the resist underlayer film and silicon-containing film-removing step may also be carried out (iv) after further etching the substrate in the etching step. In this case, since the resist underlayer film can be dissolved in the basic aqueous solution after the formation of the pattern of the substrate by etching, the resist underlayer film and the like can be conveniently removed without utilizing an ashing treatment and the like, and therefore an influence etc. of the ashing treatment and the like on the substrate can be minimized.

According to the pattern-forming method, the resist underlayer film and the silicon-containing film can be removed by dissolving the resist underlayer film in the basic aqueous solution without using the dry removal or concentrated aqueous hydrogen fluoride which may cause a severe damage to the substrate, leading to the reprocessing of the substrate. In addition, the resist underlayer film and the like can be conveniently removed without utilizing the ashing treatment and the like after the formation of the pattern of the substrate, and therefore an influence etc. of the ashing treatment and the like on the substrate can be minimized. Hereinafter, each step will be described.

Resist Underlayer Film-Forming Step

In this step, a resist underlayer film is formed on a substrate. Examples of the substrate include insulating films such as silicon oxide, silicon nitride, silicon nitride oxide and polysiloxane, as well as interlayer insulating films such as wafers coated with low-dielectric insulating film such as "Black Diamond" (AMAT), "SiLK" (Dow Chemical) and LKD5109 (JSR Corporation), which are commercially available products. Polysilicon, and metal gate films, as generally referred to, produced by implanting a metal component into the polysilicon and the like are also included. A substrate patterned so as to have wiring grooves (trenches), plug grooves (vias) or the like may also be used as the substrate.

The resist underlayer film is preferably formed from a composition for resist underlayer film formation that contains an aromatic ring-containing resin (hereinafter, may be also merely referred to as "composition for resist underlayer film formation"). The composition for resist underlayer film formation will be described later. The resist underlayer film may be formed by applying the composition for resist underlayer film formation onto the substrate to provide a coating film thereof, and subjecting the coating film to a heating treatment, or irradiation with ultraviolet light and a heating treatment to harden the coating film. The application procedure of the composition for resist underlayer film formation is exemplified by spin coating, roll coating, dip coating, and the like. The lower limit of the heating temperature is preferably 150° C., and more preferably 180° C. The upper limit of the heating temperature is preferably 350° C., more preferably 300° C., and still more preferably 270° C. When the heating temperature is greater than 350° C., the resist underlayer film tends to be difficult to be dissolved in the resist underlayer film and silicon-containing film-removing step described later. The lower limit of the heating time period is preferably 30 sec, and more preferably 45 sec. The upper limit of the heating time period is preferably 1,200 sec, and more preferably 600 sec. The lower limit of the average thickness of the resist underlayer film is preferably 10 nm. The upper limit of the average thickness is preferably 500 nm.

In addition, other underlayer film distinct from the resist underlayer film may be formed on the top face of the substrate or on the resist underlayer film. The other underlayer film is a film to which a reflection-preventing function, coating film flatness, superior etching resistance against fluorine-containing gases such as $CF_4$ and/or the like are/is imparted. The other underlayer film may be formed by using, for example, a commercially available product such as NFC HM8005 (JSR Corporation).

Composition for Resist Underlayer Film Formation

The composition for resist underlayer film formation contains an aromatic ring-containing resin (hereinafter, may be also referred to as "(A) resin" or "resin (A)"), and may further contain an optional component such as (B) a solvent. Hereinafter, each component will be described.

(A) Resin

The resin (A) is an aromatic ring-containing resin. The resin (A) is preferably a novolak resin, an acenaphthylene resin or a combination thereof (hereinafter, may be also referred to as "(A1) resin" or "resin (A1)"). In addition, a resin that contains a calixarene compound (hereinafter, may be also referred to as "(A2) compound" or "compound (A2)") is preferred as the resin (A).

(A1) Resin

The resin (A1) preferably has a structural unit represented by the following formula (1) (hereinafter, may be also referred to as "structural unit (I)").

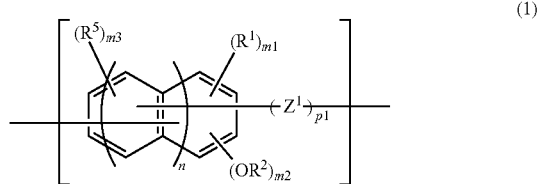

In the above formula (1), $Z^1$ represents a substituted or unsubstituted alkanediyl group, a substituted or unsubstituted arenediyl group or a substituted or unsubstituted oxyalkanediyl group; p1 represents the number of $Z^1$ that bonds to the aromatic ring, and is an integer of 1 to 10, wherein in a case where p1 is no less than 2, a plurality of $Z^1$s may be identical or different; $R^1$ and $R^5$ each independently represent a monovalent organic group having 1 to 20 carbon atoms; m1 is an integer of 0 to 6, wherein in a case where m1 is no less than 2, a plurality of $R^1$s may be identical or different; m3 is an integer of 0 to 6, wherein in a case where m3 is no less than 2, a plurality of $R^5$s may be identical or different; $R^2$ represents a hydrogen atom or a monovalent organic group having 1 to 20 carbon atoms; m2 is an integer of 1 to 8, wherein in a case where m2 is no less than 2, a plurality of $R^2$s may be identical or different; and n is an integer of 0 to 2, wherein the sum of m1, m2, m3 and p1 is no greater than 10.

Examples of the alkanediyl group of the substituted or unsubstituted alkanediyl group which may be represented by $Z^1$ include an ethanediyl group, a propanediyl group, a butanediyl group, a pentanediyl group, a hexanediyl group, a 1-methyl-1,3-propanediyl group, a 2-methyl-1,3-propanediyl group, a 2-methyl-1,2-propanediyl group, a 1-methyl-1,4-butanediyl group, a 2-methyl-1,4-butanediyl group, and the like.

Examples of the arenediyl group of the substituted or unsubstituted arenediyl group which may be represented by $Z^1$ include a phenylene group, a naphthylene group, an anthrylene group, a phenanthrylene group, and the like.

Examples of the substituted or unsubstituted oxyalkanediyl group which may be represented by $Z^1$ include an oxyethanediyl group, a 1,3-oxypropanediyl group, a 1,2-oxypropanediyl group, an oxybutanediyl group, an oxypentanediyl group, an oxyhexanediyl group, and the like.

The substituent which may be included in $Z^1$ is exemplified by a halogen atom, an alkyl group having 1 to 9 carbon atoms, an aryl group having 6 to 22 carbon atoms, and the like. Examples of the halogen atom include fluorine, chlorine, bromine, iodine, and the like. Examples of the alkyl group having 1 to 9 carbon atoms include a methyl group, an ethyl group, a n-propyl group, an i-propyl group, a n-butyl group, a 2-methylpropyl group, a 1-methylpropyl group, a t-butyl group, and the like. Examples of the aryl group having 6 to 22 carbon atoms include a phenyl group, a naphthyl group, and the like.

In the formula (1), p1 is preferably 1.

The monovalent organic group having 1 to 20 carbon atoms which is represented by $R^1$ or $R^5$ is exemplified by an alkyl group having 1 to 6 carbon atoms, an alkoxy group having 1 to 6 carbon atoms, an alkoxycarbonyl group having 2 to 10 carbon atoms, an aryl group having 6 to 14 carbon atoms, a glycidyl ether group, an alkylglycidyl ether group (wherein the number of carbon atoms of the alkyl moiety is 1 to 6), and the like.

Examples of the alkyl group having 1 to 6 carbon atoms include a methyl group, an ethyl group, a n-propyl group, an i-propyl group, a n-butyl group, a 2-methylpropyl group, a 1-methylpropyl group, a t-butyl group, and the like.

Examples of the alkoxy group having 1 to 6 carbon atoms include a methoxy group, an ethoxy group, a n-propoxy group, an i-propoxy group, a n-butoxy group, a 2-methylpropoxy group, a 1-methylpropoxy group, a t-butoxy group, and the like.

Examples of the alkoxycarbonyl group having 2 to 10 carbon atoms include a methoxycarbonyl group, an ethoxycarbonyl group, a n-propoxycarbonyl group, an i-propoxycarbonyl group, a n-butoxycarbonyl group, a 2-methylpropoxycarbonyl group, a 1-methylpropoxycarbonyl group, a t-butoxycarbonyl group, and the like.

Examples of the aryl group having 6 to 14 carbon atoms include a phenyl group, a naphthyl group, and the like.

Examples of the alkylglycidyl ether group include a methylglycidyl ether group, an ethylglycidyl ether group, a propylglycidyl ether group, a butylglycidyl ether group, and the like.

In the formula (1), m1 is preferably 0.
In the formula (1), m3 is preferably 0.

Examples of the monovalent organic group having 1 to 20 carbon atoms which may be represented by $R^2$ include monovalent organic groups having 1 to 20 carbon atoms similar to those exemplified in connection with $R^1$ and $R^5$, and the like.

$R^2$ preferably represents a hydrogen atom.

A group represented by —$R^3$—COOR$^4$ is also preferred as $R^2$, wherein $R^3$ represents a divalent organic group having 1 to 20 carbon atoms, and $R^4$ represents a tertiary alkyl group.

The divalent organic group having 1 to 20 carbon atoms which is represented by $R^3$ is exemplified by a group obtained by eliminating one hydrogen atom from the monovalent organic group having 1 to 20 carbon atoms which is exemplified in connection with $R^1$, and the like.

$R^3$ preferably represents a methanediyl group.

The tertiary alkyl group represented by $R^4$ is preferably a t-butyl group.

In the formula (1), m2 is preferably 1 or 2.
In the formula (1), n is preferably 1.

The lower limit of the polystyrene equivalent weight average molecular weight (hereinafter, may be also referred to as "Mw") of the resin (A1) is preferably 500, more preferably 1,000, and still more preferably 1,200. The upper limit of the Mw of the resin (A1) is preferably 100,000, more preferably 50,000, and still more preferably 40,000. It is to be noted that each weight average molecular weight used herein is determined by gel permeation chromatography using mono-dispersed polystyrene as a standard substance. Specific measurement conditions will be described later.

The lower limit of the polystyrene equivalent number average molecular weight (hereinafter, may be also referred to as "Mn") of the resin (A1) is preferably 400, more preferably 800, and still more preferably 1,000. The upper limit of the Mn of the resin (A1) is preferably 80,000, more preferably 40,000, and still more preferably 35,000.

The upper limit of the ratio (Mw/Mn ratio) of the Mw to the Mn of the resin (A1) is preferably 5, and more preferably 3. The lower limit of the ratio (Mw/Mn ratio) is typically 1.

Moreover, the resin composition for resist underlayer film formation according to the embodiment of the present invention may contain the resin (A1) either alone of one type, or in combination of two or more types thereof.

Synthesis Method of Resin (A1)

The resin (A1) can be synthesized by, for example, reacting a compound that includes a hydroxy group with an aldehyde by use of an acidic catalyst and the like.

(A2) Compound

Calixarene Compound

The calixarene compound is preferably a compound represented by the following formula (2).

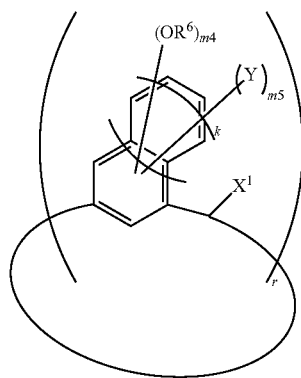

(2)

In the above formula (2), $R^6$ represents a hydrogen atom or a monovalent organic group having 1 to 30 carbon atoms; r is an integer of 4 to 12; Y represents a hydrocarbon group having 1 to 10 carbon atoms; k is 0 or 1; m4 is an integer of 1 to 3; and m5 is an integer of 0 to 7, wherein the sum of m4 and m5 is no greater than 8; and $X^1$ represents a substituted or unsubstituted monovalent hydrocarbon group having 1 to 30 carbon atoms or a hydrogen atom, wherein in a case where m4 is no less than 2, a plurality of $R^6$s may be identical or different, in a case where m5 is no less than 2, a plurality of Ys may be identical or different, and in a case where r is no less than 2, a plurality of $X^1$s may be identical or different, a plurality of ks may be identical or different, a plurality of m4s may be identical or different and a plurality of m5s may be identical or different.

The monovalent organic group having 1 to 30 carbon atoms which may be represented by $R^6$ is exemplified by: a monovalent hydrocarbon group; a group obtained by incorporating a hetero atom-containing group between two adjacent carbon atoms of the monovalent hydrocarbon group; a group obtained from the monovalent hydrocarbon group or the group obtained by incorporating a hetero atom-containing group between two adjacent carbon atoms of the monovalent hydrocarbon group, by substituting a part or all of hydrogen atoms included therein with a substituent; and the like.

The monovalent hydrocarbon group is exemplified by a monovalent chain hydrocarbon group having 1 to 30 carbon atoms, a monovalent alicyclic hydrocarbon group having 3 to 30 carbon atoms, a monovalent aromatic hydrocarbon group having 6 to 30 carbon atoms, and the like.

Examples of the monovalent chain hydrocarbon group include:

alkyl groups such as a methyl group, an ethyl group, a propyl group, a butyl group and a pentyl group;

alkenyl groups such as an ethenyl group, a propenyl group, a butenyl group and a pentenyl group;

alkynyl groups such as an ethynyl group, a propynyl group, a butynyl group and a pentynyl group; and the like.

Examples of the monovalent alicyclic hydrocarbon group include:

monocyclic cycloalkyl groups such as a cyclopropyl group, a cyclobutyl group, a cyclopentyl group and a cyclohexyl group;

unsaturated monocyclic alicyclic hydrocarbon groups such as a cyclopropenyl group, a cyclobutenyl group, a cyclopentenyl group, a cyclohexenyl group and a cyclopentadienyl group;

polycyclic cycloalkyl groups such as a norbornyl group, an adamantyl group, a tricyclodecyl group and a tetracyclododecyl group;

unsaturated polycyclic alicyclic hydrocarbon groups such as a norbornenyl group, a tricyclodecenyl group, a tetracyclododecyl group and a norbornanedienyl group; and the like.

Examples of the monovalent aromatic hydrocarbon group include:

aryl groups such as a phenyl group, a tolyl group, a xylyl group, a mesityl group, a naphthyl group, a methylnaphthyl group, an anthryl group and a methylanthryl group;

aralkyl groups such as a benzyl group, a phenethyl group, a naphthylmethyl group and an anthrylmethyl group; and the like.

Examples of the hetero atom-containing group include —O—, —S—, —NR'—, —CO—, —CS—, a combination of at least two of these groups, and the like, wherein R' represents a monovalent hydrocarbon group having 1 to 10 carbon atoms.

Examples of the group obtained by incorporating a hetero atom-containing group between two adjacent carbon atoms of the monovalent hydrocarbon group include:

chain groups such as alkoxyalkyl groups, alkylsulfanylalkyl groups, alkyliminoalkyl groups, acylalkyl groups, and alkylthiocarbonylalkyl groups; and cyclic groups such as cyclic ether groups, cyclic thioether groups, cyclic amino groups, cyclic ketone groups, and cyclic thioketone groups.

Examples of the substituent include halogen atoms such as a fluorine atom, a chlorine atom, a bromine atom and an iodine atom, a hydroxy group, a carboxy group, a cyano group, a nitro group, an alkoxy group, an alkoxycarbonyl group, an alkoxycarbonyloxy group, an acyl group, an acyloxy group, and the like.

Examples of the hydrocarbon group having 1 to 10 carbon atoms which is represented by Y include hydrocarbon groups having 1 to 10 carbon atoms among the hydrocarbon groups exemplified as the monovalent organic group in connection with $R^5$; and the like.

Of these, hydrocarbon groups having 1 to 5 carbon atoms are preferred, alkyl groups having 1 to 5 carbon atoms are more preferred, a propyl group and a butyl group are still more preferred, and a t-butyl group is particularly preferred.

In the above formula (2), m4 is preferably 2 or 3 in the case of k being 0, and preferably 1 in the case of k being 1.

In the above formula (2), m5 is preferably an integer of 0 to 2, more preferably 0 or 1, and still more preferably 0.

Examples of the substituted or unsubstituted monovalent hydrocarbon group having 1 to 30 carbon atoms which may be represented by $X^1$ include substituted or unsubstituted hydrocarbon groups having 1 to 30 carbon atoms among the substituted or unsubstituted hydrocarbon groups exemplified as the monovalent organic group, and the like.

$X^1$ represents preferably a hydrogen atom, a substituted or unsubstituted chain hydrocarbon group, or a substituted or unsubstituted aromatic hydrocarbon group, more preferably a hydrogen atom, a substituted or unsubstituted monovalent chain hydrocarbon group, or a substituted or unsubstituted monovalent aromatic hydrocarbon group, still more preferably a hydrogen atom, an alkyl group, a hydroxy-substituted phenyl group or an unsubstituted naphthyl group, and particularly preferably a hydrogen atom, a propyl group, a 4-hydroxyphenyl group, a 3,4-dihydroxyphenyl group, a 3,4,5-trihydroxyphenyl group or a 2-naphthyl group.

The lower limit of r is preferably 4, and more preferably 5. The upper limit of r is preferably 8, more preferably 7, and still more preferably 6.

The lower limit of the molecular weight of the compound (A2) is preferably 500, more preferably 700, and still more preferably 1,000. The upper limit of the molecular weight of the compound (A2) is preferably 3,000, more preferably 2,500, and still more preferably 2,200.

The lower limit of the content of the compound (A2) in the composition for resist underlayer film formation with respect to the total solid content is preferably 80% by mass, more preferably 90% by mass, and still more preferably 95% by mass.

Synthesis Method of Compound (A2)

The compound (A2) can be synthesized by, for example, a condensation reaction of a hydroxy compound represented by the following formula (a1) with an aldehyde compound represented by the following formula (a2).

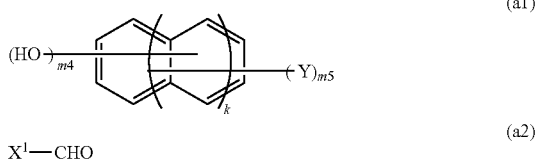

(a1)

$X^1$—CHO (a2)

In the above formula (a 1), m4, k, Y and m5 are as defined in the above formula (2).

In the above formula (a2), $X^1$ is as defined in the above formula (2).

(B) Solvent

The solvent (B) is not particularly limited as long as it can dissolve the resin (A), and is exemplified by an alcohol solvent, an ether solvent, a ketone solvent, an amide solvent, an ester solvent, a hydrocarbon solvent, and the like.

Examples of the alcohol solvent include monohydric alcohol solvents having 1 to 18 carbon atoms, polyhydric alcohol solvents having 2 to 18 carbon atoms, polyhydric alcohol partial ether solvents having 3 to 19 carbon atoms, and the like.

Examples of the ether solvent include:
dialkyl ether solvents such as diethyl ether, dipropyl ether and dibutyl ether;
cyclic ether solvents such as tetrahydrofuran and tetrahydropyran;
aromatic ring-containing ether solvents such as diphenyl ether and anisole; and the like.

Examples of the ketone solvent include:
chain ketone solvents such as acetone, methyl ethyl ketone, methyl n-propyl ketone, methyl n-butyl ketone, diethyl ketone, methyl iso-butyl ketone, methyl n-pentyl ketone, ethyl n-butyl ketone, methyl n-hexyl ketone, di-iso-butyl ketone and trimethylnonanone;
cyclic ketone solvents such as cyclopentanone, cyclohexanone, cycloheptanone, cyclooctanone and methylcyclohexanone;
2,4-pentanedione, acetonylacetone and acetophenone; and the like.

Examples of the amide solvent include:
cyclic amide solvents such as N,N'-dimethylimidazolidinone and N-methylpyrrolidone;
chain amide solvents such as N-methylformamide, N,N-dimethylformamide, N,N-diethylformamide, acetamide, N-methylacetamide, N,N-dimethylacetamide and N-methylpropionamide; and the like.

Examples of the ester solvent include: carboxylic acid ester solvents, e.g., monocarboxylic acid ester solvents such as ethyl acetate and ethyl lactate, polyhydric carboxylic acid ester solvents such as diethyl malonate and diethyl phthalate, and the like; polyhydric alcohol partial ether carboxylate solvents, e.g., polyhydric alcohol partial ether acetate solvents such as propylene glycol monomethyl ether acetate, and the like; lactone solvents such as butyrolactone and valerolactone; carbonate solvents such as dimethyl carbonate, diethyl carbonate, ethylene carbonate and propylene carbonate; and the like.

Examples of the hydrocarbon solvent include aliphatic hydrocarbon solvents having 5 to 12 carbon atoms, aromatic hydrocarbon solvents having 6 to 16 carbon atoms, and the like.

Of these, an ester solvent and a ketone solvent are preferred, a polyhydric alcohol partial ether carboxylate solvent, a carboxylic acid ester solvent and a ketone solvent are more preferred, a polyhydric alcohol partial ether acetate solvent, a monocarboxylic acid ester solvent and a cyclic ketone solvent are still more preferred, propylene glycol monomethyl ether acetate, ethyl lactate and cyclohexanone are particularly preferred, and propylene glycol monomethyl ether acetate is further particularly preferred. The composition for resist underlayer film formation may contain one type, or two or more types of the solvent (B).

Other Optional Component

The composition for resist underlayer film formation may contain other optional component in addition to the components (A) and (B). The other optional component is exemplified by an acid generating agent, a crosslinking agent, a surfactant, and the like. Each of the other optional components may be used either alone of one type, or in combination of two or more types thereof.

Acid Generating Agent

The acid generating agent is a component that is capable of generating an acid upon an exposure or heating. When the composition for resist underlayer film formation contains the acid generating agent, crosslinking of molecules of the resin (A) can be allowed more effectively at comparatively low temperatures including normal temperature.

An acid generating agent that is capable of generating an acid upon an exposure (hereinafter, may be also referred to as "photoacid generating agent") is exemplified by acid generating agents disclosed in paragraphs [0077] to [0081] of Japanese Unexamined Patent Application, Publication No. 2004-168748, and the like.

Among these photoacid generating agents, diphenyliodonium trifluoromethanesulfonate, diphenyliodonium nonafluoro-n-butanesulfonate, diphenyliodonium pyrenesulfonate, diphenyliodonium n-dodecylbenzenesulfonate, diphenyliodonium 10-camphorsulfonate, diphenyliodonium naphthalenesulfonate, bis(4-t-butylphenyl)iodonium trifluoromethanesulfonate, bis(4-t-butylphenyl)iodonium nonafluoro-n-butanesulfonate, bis(4-t-butylphenyl)iodonium n-dodecylbenzenesulfonate, bis(4-t-butylphenyl)iodonium 10-camphorsulfonate and bis(4-t-butylphenyl)iodonium naphthalenesulfonate are preferred.

It is to be noted that these photoacid generating agents may be used either alone of one type, or in combination of two types thereof.

In addition, an acid generating agent that is capable of generating an acid upon heating (hereinafter, may be also referred to as "thermal acid generating agent") is exemplified by 2,4,4,6-tetrabromocyclohexadienone, benzoin tosylate, 2-nitrobenzyl tosylate, alkylsulfonates, and the like.

It is to be noted that these thermal acid generating agents may be used either alone of one type, or in combination of two or more types thereof. In addition, the photoacid generating agent and the thermal acid generating agent may be used in combination as the acid generating agent.

When the composition for resist underlayer film formation contains the acid generating agent, the lower limit of the content of the acid generating agent with respect to 100 parts by mass of the resin (A) of the composition for resist underlayer film formation is preferably 0.1 parts by mass. The upper limit of the content of the acid generating agent is preferably 5,000 parts by mass, preferably 1,000 parts by mass more, and still more preferably 100 parts by mass.

Crosslinking Agent

The crosslinking agent is a compound that includes a crosslinkable group (except for a compound falling under the category of the resin (A)). When the composition for resist underlayer film formation contains the crosslinking agent, crosslinking of the resin (A) can be allowed more effectively.

The crosslinking agent preferably includes at least two crosslinkable groups. The crosslinking agent is exemplified by methoxymethylated melamines such as hexakis(methoxymethyl)melamine, methoxymethylated glycolurils such as tetrakis(methoxymethyl)glycoluril, and multinuclear phenol compounds such as 2,2',6,6'-tetrakis(methoxymethyl)-4,4'-(1-(4-(2-(3,5-bis(methoxymethyl)-4-hydroxyphenyl)-2-propyl)phenyl)ethylidene)bisphenol. Of these, methoxymethylated glycolurils and multinuclear phenol compounds are preferred. The crosslinking agent is not limited and may be selected in accordance with the type of the resin (A) and/or required characteristics; in a case where the resin (A1) is used as the resin (A), the crosslinking agent is preferably methoxymethylated glycoluril, whereas in a case where the compound (A2) is used, the crosslinking agent is preferably a multinuclear phenol compound.

When the composition for resist underlayer film formation contains the crosslinking agent, the lower limit of the content of the crosslinking agent with respect to 100 parts by mass of the resin (A) is preferably 5 parts by mass, and more preferably 30 parts by mass. The upper limit of the content of the crosslinking agent is preferably 1,000 parts by mass, more preferably 700 parts by mass, and still more preferably 500 parts by mass. The crosslinking agent may be used either alone of one type, or in combination of two or more types thereof.

Surfactant

The surfactant is a component having a function of improving application property, striation, wettability, developability, and the like. The upper limit of the content of the surfactant with respect to 100 parts by mass of the resin (A) is preferably 15 parts by mass, and more preferably 10 parts by mass. The surfactant may be used either alone of one type, or in combination of two or more types thereof.

Preparation Method of Composition for Resist Underlayer Film Formation

The composition for resist underlayer film formation may be prepared by, for example, mixing the resin (A), the solvent (B), and optional component contained as needed at a predetermined ratio. The composition for resist underlayer film formation is preferably filtered through a filter of 0.1 μm, for example, after the mixing. The lower limit of the solid content concentration of the composition for resist underlayer film formation is preferably 0.1% by mass, more preferably 0.5 parts by mass, and still more preferably 1 part by mass. The upper limit of the solid content concentration of the composition for resist underlayer film formation is preferably 50% by mass, more preferably 30% by mass, and still more preferably 20% by mass. The lower limit of the concentration of the resin (A) in the composition for resist underlayer film formation is preferably 0.1% by mass, more preferably 0.5% by mass, and still more preferably 1 part by mass. The upper limit of the concentration of the basic aqueous solution is preferably 30% by mass, more preferably 20% by mass, and still more preferably 15% by mass.

Silicon-Containing Film-Forming Step

In this step, a silicon-containing film is formed on an upper face side of the resist underlayer film. The silicon-containing film is provided by, for example, applying a composition for silicon-containing film formation and the like onto the resist underlayer film. The composition for silicon-containing film formation will be described later. The application procedure of the composition for silicon-containing film formation is exemplified by spin-coating, cast coating, roll coating, and the like. It is to be noted that the lower limit of the average thickness of the formed silicon-containing film is preferably 10 nm, and more preferably 20 nm. The upper limit of the average thickness of the formed silicon-containing film is preferably 1,000 nm, more preferably 500 nm, and still more preferably 300 nm.

The composition for silicon-containing film formation contains (C) polysiloxane and (B2) an organic solvent. The composition for silicon-containing film formation may contain other optional component such as a crosslinking accelerator as a favorable component within a range not leading to impairment of the effects of the present invention. Hereinafter, each component will be described.

(C) Polysiloxane

The structure of the polysiloxane (C) is not particularly limited, and the polysiloxane (C) is preferably a hydrolytic condensation product of at least one selected from silane compounds represented by the following formulae (3) to (6). When such polysiloxane (C) is used, the pattern collapse resistance of the formed resist pattern can be improved.

$$R^7_a SiX^2_{4-a} \tag{3}$$

In the above formula (3), $R^7$ represents a hydrogen atom, a fluorine atom, an alkyl group having 1 to 5 carbon atoms, a cyano group, a cyanoalkyl group, an alkylcarbonyloxy group, an acid anhydride group, an alkenyl group, an aryl group or an aralkyl group, wherein the alkyl group may be substituted with a fluorine atom, and the aryl group and the aralkyl group may be substituted; $X^2$ represents a halogen atom or $-OR^8$, wherein $R^8$ represents a monovalent organic group; and a is an integer of 0 to 3, wherein in a case where $R^7$ is present in a plurality of number, a plurality of $R^7$s may be identical or different, and wherein in a case where $X^2$ is present in a plurality of number, a plurality of $X^2$s may be identical or different.

Examples of the alkyl group having 1 to 5 carbon atoms which may be represented by $R^7$ include: linear alkyl groups such as a methyl group, an ethyl group, a n-propyl group, a n-butyl group and a n-pentyl group; branched alkyl groups such as an isopropyl group, an isobutyl group, a sec-butyl group, a t-butyl group and an isoamyl group; and the like.

Examples of the fluorine atom-substituted alkyl group having 1 to 5 carbon atoms which may be represented by $R^7$ include a fluoromethyl group, a difluoromethyl group, a trifluoromethyl group, a fluoroethyl group, a difluoroethyl group, a trifluoroethyl group, a perfluoroethyl group, a perfluoro-n-propyl group, a hexafluoro-i-propyl group, a perfluorobutyl group, and the like.

Examples of the cyanoalkyl group which may be represented by $R^7$ include a cyanoethyl group, a cyanopropyl group, and the like.

Examples of the alkylcarbonyloxy group which may be represented by $R^7$ include a methylcarbonyloxy group, an ethylcarbonyloxy group, a propylcarbonyloxy group, a butylcarbonyloxy group, and the like.

Examples of the alkenyl group which may be represented by $R^7$ include a group represented by the following formula (i-1), and the like.

$$CH_2=CH-(CH_2)_n-* \qquad (i\text{-}1)$$

In the above formula (i-1), n is an integer of 0 to 4; and * denotes a binding site. In the formula (i-1), n is preferably 0 or 1, and more preferably 0 (i.e., vinyl group).

Examples of the aryl group which may be represented by $R^7$ include a phenyl group, a naphthyl group, a methylphenyl group, an ethylphenyl group, and the like.

Examples of the aralkyl group which may be represented by $R^7$ include a benzyl group, a phenylethyl group, a phenylpropyl group, a naphthylmethyl group, and the like.

Examples of the substituent which may be included in the aryl group or the aralkyl group include halogen atoms such as a fluorine atom, a chlorine atom, a bromine atom and an iodine atom, a hydroxyl group, a carboxyl group, a cyano group, a nitro group, an alkoxy group, an aryloxy group, an acyl group, an amino group, a substituted amino group, and the like.

Examples of the halogen atom which may be represented by $X^2$ include a fluorine atom, a chlorine atom, and the like.

Examples of the monovalent organic group represented by $R^8$ in $-OR^8$ include alkyl groups having 1 to 4 carbon atoms such as a methyl group, an ethyl group, a n-propyl group, an isopropyl group, a n-butyl group, an isobutyl group, a sec-butyl group and a t-butyl group, and the like. In the formula (3), a is preferably an integer of 0 to 2.

$$R_bSi(OR^9)_{4-b} \qquad (4)$$

In the above formula (4), R represents a hydrogen atom, a fluorine atom or a monovalent organic group; and $R^9$ represents a monovalent organic group, and b is an integer of 1 to 2.

The monovalent organic group represented by R or $R^9$ is exemplified by an alkyl group, an aryl group, an allyl group, a glycidyl group, a vinyl group, and the like. In the above formula (4), R represents preferably a monovalent organic group, and more preferably an alkyl group or a phenyl group. In this regard, examples of the alkyl group include a methyl group, an ethyl group, a propyl group, a butyl group, and the like. The alkyl group preferably has 1 to 5 carbon atoms, and may be a chain alkyl group or a branched alkyl group. Further, a hydrogen atom of the alkyl group may be substituted with a fluorine atom or the like. In the above formula (4), examples of the aryl group include a phenyl group, a naphthyl group, a methylphenyl group, an ethylphenyl group, a chlorophenyl group, a bromophenyl group, a fluorophenyl group, and the like.

$$Si(OR^{10})_4 \qquad (5)$$

In the above formula (5), $R^{10}$ represents a monovalent organic group.

Examples of the monovalent organic group represented by $R^{10}$ include monovalent organic groups similar to those exemplified in connection with R and $R^9$ in the above formula (4), and the like.

$$R^{11}{}_c(R^{12}O)_{3-c}Si-(R^{15})_e-Si(OR^{13})_{3-d}R^{14}{}_d \qquad (6)$$

In the above formula (6), $R^{11}$ to $R^{14}$ are identical to or different from each other, and each independently represent a monovalent organic group; c and d are identical to or different from each other and are 0 to 2; $R^{15}$ represents an oxygen atom, a phenylene group or a group represented by $-(CH_2)_n-$, wherein n is an integer of 1 to 6; and e is 0 or 1.

Examples of the monovalent organic group represented by $R^{11}$ to $R^{14}$ include monovalent organic groups similar to those exemplified in connection with R and $R^9$ in the above formula (4), and the like.

The polysiloxane (C) may be contained in the composition for silicon-containing film formation either alone of one type, or in combination of two or more types thereof.

The lower limit of the polystyrene equivalent weight average molecular weight (Mw) of the polysiloxane (C) as determined by gel permeation chromatography (GPC) is preferably 1,000, more preferably 1,200, and still more preferably 1,500. The upper limit of the Mw of the polysiloxane (C) is preferably 20,000, more preferably 15,000, still more preferably 10,000, and particularly preferably 7,000.

A well-known method for hydrolytic condensation may be used for the method for hydrolytic condensation of the silane compound (3) and other silane compound used as needed.

The lower limit of the content of the polysiloxane (C) with respect to the total solid content of the composition for silicon-containing film formation is preferably 70% by mass, more preferably 80% by mass, and still more preferably 90% by mass.

(B2) Organic Solvent

The composition for silicon-containing film formation contains the organic solvent (B2). The organic solvent (B2) is not particularly limited as long as it can dissolve or disperse the polysiloxane (C) and optional component described later. The organic solvent (B2) is exemplified by solvents similar to those exemplified in connection with the solvent (B), and the like.

The organic solvent (B2) is preferably propylene glycol monomethyl ether, propylene glycol monoethyl ether or propylene glycol monomethyl ether acetate.

Optional Component
  Crosslinking Accelerator
  The crosslinking accelerator is a compound that is capable of accelerating a crosslinking reaction between the molecular chains of the polysiloxane (C) or within the molecular chain thereof, in forming the silicon-containing film from the composition for silicon-containing film formation, for example. The crosslinking accelerator is not particularly limited as long as it has the aforementioned property, and conventionally well-known crosslinking accelerators may be used; examples thereof include acids, bases, metal complexes, metal salt compounds, onium salt compounds, and the like. The crosslinking accelerator may be used either alone of one type, or in combination of two or more types thereof.

The composition for silicon-containing film formation may further contain, in addition to the components described above, an acid generating agent, a base generating agent, a surfactant, β-diketone, colloidal silica, colloidal alumina, an organic polymer, and the like, as an optional component.

Preparation Method of Composition for Silicon-Containing Film Formation

The composition for silicon-containing film formation may be obtained by, for example, mixing the polysiloxane (C), the organic solvent (B2) and the optional component as needed, and dissolving or dispersing the mixture in the organic solvent (B2). The lower limit of the solid content concentration of the composition for silicon-containing film formation is preferably 0.5% by mass, and more preferably 1% by mass. The upper limit of the solid content concentration of the composition for silicon-containing film formation is preferably 20% by mass, more preferably 15% by mass, and still more preferably 10% by mass.

The lower limit of the contact angle of pure water on the silicon-containing film is preferably 40°, and more preferably 45°. The upper limit of the contact angle is preferably 80°, and more preferably 75°. It is to be noted that the contact angle as referred to herein is measured at 25° C., unless otherwise specified particularly. When the contact angle on the silicon-containing film falls within the above range, favorable wet spreadability of a basic aqueous solution in the resist underlayer film and silicon-containing film-removing step described later, and/or favorable adhesiveness of the resist pattern typically formed on the silicon-containing film can be exhibited.

The silicon-containing film is preferably formed from a hydrolytic condensation product of a compound including a tetrafunctional silane monomer in an amount of no less than 60 mol %. It is to be noted that the tetrafunctional silane monomer as referred to herein means a silane monomer having four hydrolyzable groups on the silicon atom. The hydrolyzable group is exemplified by an alkoxy group, an aryloxy group, a halogeno group and the like. The trifunctional silane monomer, the bifunctional silane monomer, and the like are similarly defined with respect to each corresponding number of hydrolyzable groups.

After the composition for silicon-containing film formation is applied, prebaking (PB) may be carried out to evaporate a solvent in the coating film, as needed. The PB temperature may be appropriately selected depending on the formulation of the composition for silicon-containing film formation, and the lower limit thereof is preferably 50° C., and more preferably 80° C. The upper limit of the PB temperature is preferably 450° C., and more preferably 300° C. The lower limit of the PB time period is preferably 5 sec, and more preferably 10 sec. The upper limit of the PB time period is preferably 600 sec, and more preferably 200 sec.

Resist Underlayer Film and Silicon-Containing Film-Removing Step

In this step, at least a part of the resist underlayer film and at least a part of the silicon-containing film are removed with a basic aqueous solution. According to this step, the resist underlayer film and the silicon-containing film can be removed by dissolving the resist underlayer film without causing a severe damage to the substrate and reprocessing of the substrate is enabled. A procedure for the dissolution of the resist underlayer film in the basic aqueous solution is not particularly limited as long as the resist underlayer film and the basic aqueous solution are brought into contact with each other for a certain time period, and the procedure for the dissolution of the resist underlayer film is exemplified by: a procedure that involves immersion of the substrate having the resist underlayer film and the silicon-containing film formed thereon in the basic aqueous solution; a procedure that involves spraying of the basic aqueous solution; a procedure that involves application (or coating) of the basic aqueous solution, and the like. It is to be noted that the lower limit of the immersion time period in the immersion procedure is preferably 0.2 min. The upper limit of the immersion time period is preferably 30 min. In addition, this step is preferably carried out at a temperature of less than 100° C. In each procedure, it is preferred that the substrate is washed with water and dried after the completion of the procedure.

The basic aqueous solution is not particularly limited as long as it is basic, and a basic aqueous solution of, for example, sodium hydroxide, potassium hydroxide, sodium carbonate, sodium silicate, sodium metasilicate, ammonia, ethylamine, n-propylamine, diethylamine, di-n-propylamine, triethylamine, methyl diethylamine, dimethylethanolamine, triethanolamine, tetramethylammonium hydroxide (TMAH), tetraethylammonium hydroxide, pyrrole, piperidine, choline, 1,8-diazabicyclo[5.4.0]-7-undecene, 1,5-diazabicyclo[4.3.0]-5-nonene, and/or the like may be used. Of these, a basic aqueous solution that contains none of hydrogen fluoride, a salt thereof, and a salt of a fluorine compound is preferred as the basic aqueous solution. Moreover, a liquid containing tetraalkylammonium hydroxide and water, and a liquid obtained by mixing ammonia, hydrogen peroxide and water are preferred as the basic aqueous solution. The liquid obtained by mixing ammonia, hydrogen peroxide and water is not particularly limited as long as it is obtained by mixing ammonia, hydrogen peroxide and water, and includes a liquid that is obtained by mixing ammonia, hydrogen peroxide and water but does not allow detection of ammonia and/or hydrogen peroxide due to a reaction of ammonia with hydrogen peroxide, and the like. In other words, the liquid obtained by mixing ammonia, hydrogen peroxide and water is a liquid that contains water, with ammonia and hydrogen peroxide, and/or a reaction product of ammonia and hydrogen peroxide. Specific examples of the liquid obtained by mixing ammonia, hydrogen peroxide and water include: a liquid that contains ammonia, hydrogen peroxide and water; a liquid that contains a reaction product of ammonia and hydrogen peroxide, ammonia and water; a liquid that contains a reaction product of ammonia and hydrogen peroxide, hydrogen peroxide and water; a liquid that contains a reaction product of ammonia and hydrogen peroxide, and water; and the like. Of these, a liquid that contains ammonia, hydrogen peroxide and water is preferred. In addition, the basic aqueous solution may contain an appropriate amount of a water soluble organic solvent, e.g., alcohols such as methanol and ethanol, and a surfactant. Further, the basic aqueous solution may contain an organic solvent in addition to water as long as the solution is basic.

The lower limit of the ratio of hydrogen peroxide contained to the nitrogen compound in the basic aqueous solution is preferably 1/500. The upper limit of the ratio of hydrogen peroxide contained to the nitrogen compound in the basic aqueous solution is preferably 500. When the ratio of hydrogen peroxide contained to the nitrogen compound in the basic aqueous solution falls within the above range, the removability of the resist underlayer film with the basic aqueous solution can be further improved.

The lower limit of the pH of the basic aqueous solution is preferably 7.5, and more preferably 8. When the pH is less than 7.5, the resist underlayer film may not be removed sufficiently.

In addition, the lower limit of the water content in the basic aqueous solution is preferably 40% by mass, more preferably 60% by mass, and still more preferably 80% by mass.

The lower limit of the concentration of the basic aqueous solution is preferably 0.1% by mass, and more preferably 0.5% by mass. The upper limit of the concentration of the basic aqueous solution is preferably 40% by mass, and more preferably 30% by mass.

Resist Pattern-Forming Step

In this step, a resist pattern is formed on the silicon-containing film formed in the silicon-containing film-forming step. As the procedure for forming the resist pattern in this step, conventionally well-known procedures such as a procedure involving the use of a resist composition and a procedure involving the use of a nanoimprint lithography process, for example, can be employed.

Etching Step

In this step, the silicon-containing film is etched using the resist pattern as a mask such that the silicon-containing film has a pattern. According to the pattern-forming method, since the resist film not patterned properly and the silicon-containing film not patterned properly can be removed together with the resist underlayer film in the aforementioned resist underlayer film and silicon-containing film-removing step even after the etching, the resist underlayer film, the silicon-containing film and the resist film can be re-formed, leading to refabrication.

In this step, the step of further etching the resist underlayer film such that the resist underlayer film has a pattern may be included. Subsequently, since the resist underlayer film is dissolved in the aforementioned resist underlayer film and silicon-containing film-removing step, the substrate can be reused.

In this step, the step of further etching the substrate may be included. Thus, the resist underlayer film can be dissolved with the basic aqueous solution after the etching of the substrate such that the substrate has a pattern. Consequently, the resist film can be removed without using an ashing treatment and the like, and an influence etc. of the ashing treatment and the like on the substrate can be minimized.

In the etching, one or more times of dry etching may be suitably carried out. The dry etching may be carried out using a well-known dry etching apparatus. As a source gas in the dry etching, oxygen atom-containing gases such as $O_2$, CO and $CO_2$, inert gases such as He, $N_2$ and Ar, chlorine-containing gases such as $Cl_2$ and $BCl_3$, fluorine-containing gases such as $CHF_3$ and $CF_4$, other gases such as $H_2$ and $NH_3$, and the like may be used depending on the elemental composition of the substance to be etched. It is to be noted that these gases may be used in combination.

Resin

A resin according to another embodiment of the present invention has a structural unit represented by the following formula (1-1).

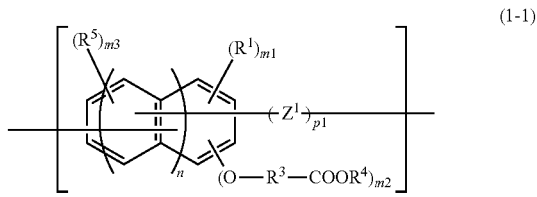

(1-1)

Since the resin has the specified structural unit, a composition for resist underlayer film formation that contains the resin is superior in solubility in the basic aqueous solution. Therefore, the resin can be suitably used as a polymer component of the composition for resist underlayer film formation used in the pattern-forming method according to the embodiment of the present invention.

The description of "(A1) Resin" in the section of "Composition for Resist Underlayer Film Formation" can be applied to the resin represented by the formula (1-1) (i.e., the resin (A1) wherein $R^2$ in the formula (1) represents —$R^3$—$COOR^4$).

Composition for Resist Underlayer Film Formation

A composition for resist underlayer film formation according to still another embodiment of the present invention contains the resin having the structural unit represented by the above formula (1-1). Due to containing the resin having the specified structure, the composition for resist underlayer film formation is superior in solubility in the basic aqueous solution. Therefore, the composition for resist underlayer film formation can be suitably used in the pattern-forming method according to the embodiment of the present invention.

EXAMPLES

Hereinafter, the present invention is explained in detail by way of Examples, but the present invention is not in any way not limited to the following Examples. Measuring methods for various types of physical properties are shown below.

Structure Confirmation of Compound

The structure of the compound was confirmed based on: the molecular weight thereof as determined by means of MALDI-TOF-MS (SHIMAZU/KRATOS matrix-assisted laser desorption/ionization time-of-flight mass spectrometer ("KOMPACT MALDI IV tDE" available from Shimadzu Corporation); an infrared absorption spectrum (IR) recorded on FT-IR ("model 420" available from JASCO Corporation); and $^1$H-NMR recorded on a nuclear magnetic resonance apparatus ("model JNM-ECA-500" available from JEOL, Ltd.) with a solvent for measurement of DMSO-d6.

Weight Average Molecular Weight (Mw)

The weight average molecular weight (Mw) was determined by gel permeation chromatography using mono-dispersed polystyrene as a standard. G2000 HXL×2 and G3000 HXL×1 (available from Tosoh Corporation) were used as GPC columns, a differential refractometer was used as a detector, and tetrahydrofuran was used as an eluent. The flow rate was 1.0 mL/min, and the column temperature was 40° C.

Synthesis of Resin (A)

Example 1

Into a 1,000 mL three-neck eggplant shaped flask were charged 100 g of 2,7-dihydroxynaphthalene, 50.7 g of formaldehyde and 300 g of methyl isobutyl ketone, and dissolution was attained at room temperature in a nitrogen atmosphere. To the resulting solution was charged 3.58 g of paratoluenesulfonic acid at the solution temperature of 40° C., and the solution temperature was elevated to 80° C. followed by aging at that temperature for 11 hrs. After the aging, the flask was cooled until the solution temperature reached room temperature. Thereafter, the reddish brown solid precipitated was collected by filtration to remove the ethanol solution. Washing with a flowing mixed solution of methanol and water (each 300 g) was carried out, followed by drying at 60° C. overnight under reduced pressure, whereby 46.5 g of pink solid matter having a hydroxy group as a terminal group was obtained. $^1$H-NMR confirmed that an intended precursor X was obtained. Next, in a 500 mL round-bottom flask, 10.0 g of the precursor X thus obtained was dissolved in 200 mL of methyl isobutyl ketone in a nitrogen atmosphere with stirring with a magnetic stirrer. After 21.4 g of t-butyl bromoacetate was added to the resulting solution under stirring, 28.4 g of potassium carbonate was further added, and the reaction was allowed at 80° C. for 18 hrs. After the completion of the reaction, the reaction solution was added to 2 L of water to which 14 mL of acetic acid was added. The supernatant liquid was removed, then the residual highly viscous matter was dissolved in a minimum amount of acetone, and the solution was charged into 500 mL of water to permit reprecipitation. The highly viscous matter thus obtained was dried at 65° C. overnight under reduced pressure, whereby 13.5 g of a resin (A-1) as a brown solid was obtained.

Synthesis Example 1

Into a 1,000 mL three-neck eggplant shaped flask were charged 100 g of 2,7-dihydroxynaphthalene, 50.7 g of formaldehyde and 300 g of ethanol, and dissolution was attained at room temperature in a nitrogen atmosphere. To the resulting solution was added dropwise 95.6 g of concentrated hydrochloric acid over 1 hour at the solution temperature of 40° C., and the solution temperature was elevated to 80° C. followed by aging at that temperature for 11 hrs. After the aging, the flask was cooled until the solution temperature reached room temperature. Thereafter, the reddish brown solid precipitated was collected by filtration to remove the ethanol solution. Washing with a flowing mixed solution of methanol and water (each 300 g) was carried out, followed by drying at 60° C. overnight under reduced pressure, whereby 45.6 g of pink solid matter having a hydroxy group as a terminal group was obtained. $^1$H-NMR confirmed that an intended resin (A-2) was obtained.

Synthesis of Polysiloxane (C)

Synthesis Example 2

An aqueous oxalic acid solution was prepared by mixing 16.19 g of 10% by mass oxalic acid and 9.72 g of water. Thereafter, a flask containing 39.43 g of tetraethoxysilane, 4.69 g of phenyltrimethoxysilane, 7.20 g of 3-(triethoxysilyl)propylsuccinic anhydride and 22.77 g of methanol was equipped with a condenser, and a dropping funnel containing the aqueous oxalic acid solution prepared as described above. Subsequently, after the flask was heated to 60° C. with an oil bath, the aqueous oxalic acid solution was slowly added dropwise, and the reaction was allowed at 60° C. for 4 hrs. After the completion of the reaction, the flask containing the reaction solution was allowed to cool, then substitution with propylene glycol monomethyl ether acetate was carried out, and methanol was removed on an evaporator, whereby 230 g of a resin solution was obtained. The solid matter in this resin solution was designated as polysiloxane (C-1). The proportion of the solid matter contained in the resin solution thus obtained was determined by a baking method, and consequently found to be 7.5% by mass. In addition, the polysiloxane (C-1) had the Mw of 2,100.

Synthesis Example 3

An aqueous oxalic acid solution was prepared by mixing 138.66 g of 10% by mass oxalic acid and 13.94 g of water. Thereafter, a flask containing 208.76 g of tetramethoxysilane, 86.22 g of methyltrimethoxysilane, 22.40 g of 4-tolyltrimethoxysilane and 230.02 g of methanol was equipped with a condenser, and a dropping funnel containing the aqueous oxalic acid solution prepared as described above. Subsequently, after the flask was heated to 60° C. with an oil bath, the aqueous oxalic acid solution was slowly added dropwise, and the reaction was allowed at 60° C. for 4 hrs. After the completion of the reaction, the flask containing the reaction solution was allowed to cool, then dilution with propylene glycol monomethyl ether acetate was carried out, and methanol was removed on an evaporator, whereby 1,610 g of a resin solution was obtained. The solid matter in this resin solution was designated as polysiloxane (C-2). The proportion of the solid matter contained in the resin solution thus obtained was determined by a baking method, and consequently found to be 7.5% by mass. In addition, the polysiloxane (C-2) had the Mw of 3,000.

Preparation of Composition for Resist Underlayer Film Formation and Composition for Silicon-Containing Film Formation Each component used in the preparation of the composition for resist underlayer film formation and the composition for silicon-containing film formation is shown below.

Solvent

B-1: propylene glycol monomethyl ether acetate
B-2: propylene glycol monomethyl ether

Example 2: Preparation of Composition for Resist Underlayer Film Formation (U-1)

A mixed solution was obtained by dissolving 5 parts by mass of the resin (A-1) obtained in Example 1 in 95 parts by mass of propylene glycol monomethyl acetate (solvent (B-1)). Thereafter, this mixed solution was filtered through a membrane filter having a pore size of 0.1 μm, whereby a composition for resist underlayer film formation (U-1) was prepared.

Synthesis Example 4: Preparation of Composition for Resist Underlayer Film Formation (U-2)

A composition for resist underlayer film formation (U-2) was prepared in a similar manner to Example 2 except that the type and the content of each component used were as specified in Table 1. It is to be noted that "–" in Table 1 indicates the absence of the corresponding component.

Synthesis Example 5: Preparation of Composition for Silicon-Containing Film Formation (U-3)

A mixed solution was obtained by dissolving 2 parts by mass of the polysiloxane (C-1) obtained in Synthesis Example 2 in 98 parts by mass of propylene glycol monomethyl ether (solvent (B-2)). Thereafter, this mixed solution was filtered through a membrane filter having a pore size of 0.1 μm, whereby a composition for silicon-containing film formation (U-3) was prepared.

Synthesis Example 6: Preparation of Composition for Silicon-Containing Film Formation (U-4)

A composition for silicon-containing film formation (U-4) was prepared in a similar manner to Synthesis Example 5 except that the type and the content of each component used were as specified in Table 1.

TABLE 1

| Composition for resist underlayer film formation/ composition for silicon-containing film formation | (A) Resin/ (C) polysiloxane | | Solvent | |
|---|---|---|---|---|
| | type | content (parts by mass) | type | content (parts by mass) |
| Example 2 | U-1 | A-1 | 5 | B-1 | 95 |
| Synthesis Example 4 | U-2 | A-2 | 5 | B-1 | 95 |
| Synthesis Example 5 | U-3 | C-1 | 2 | B-2 | 98 |
| Synthesis Example 6 | U-4 | C-2 | 2 | B-2 | 98 |

Formation of Resist Underlayer Film

Examples 3 to 6

Each composition for resist underlayer film formation and each composition for silicon-containing film formation which were prepared as described above were applied onto a silicon wafer coated with a silicon oxide film (substrate) according to a spin coating procedure. Thereafter, each "substrate having a resist underlayer film" (Examples 3 and 4), and each "substrate having a resist underlayer film and a silicon-containing film" (Example 5 and Example 6) were obtained in an ambient air atmosphere under the baking condition specified in Table 2. The average thickness of the resist underlayer film was 120 nm, and the average thickness of the silicon-containing film was 25 nm.

TABLE 2

| | Composition for resist underlayer film formation | Resist underlayer film baking (° C./60 sec) | Composition for silicon-containing film formation | Silicon-containing film baking (° C./60 sec) |
|---|---|---|---|---|
| Example 3 | U-1 | 250 | — | — |
| Example 4 | U-2 | 250 | — | — |
| Example 5 | U-1 | 250 | U-3 | 220 |
| Example 6 | U-2 | 250 | U-4 | 220 |

Evaluations

Evaluations for the following items were made according to the following methods using each substrate obtained as described above. The results of the evaluations are shown in Table 3.

Solvent Resistance

Each substrate obtained as described above was immersed in cyclohexanone (at room temperature) for 10 sec. The film thickness was measured before and after the immersion using a spectroscopic ellipsometer ("UV1280E" available from KLA-TENCOR), and a rate of change of the film thickness was calculated from the measurement values. The rate of change of the film thickness was calculated according to the following formula (a):

rate of change of film thickness (%)=100×(absolute value of the difference between the average thickness of the film after immersion and the average thickness of the film before immersion)/(the average thickness of the film before immersion) (a)

The solvent resistance was evaluated to be: "A" (favorable) in the case of the rate of change of the film thickness being less than 1%; and "B" (unfavorable) in the case of the rate of change of the film thickness being no less than 1%.

Solubility in TMAH Developer Solution

Each substrate obtained as described above was immersed in a 2.38% by mass TMAH developer solution for 60 sec. The film thickness was measured before and after the immersion using a spectroscopic ellipsometer ("UV1280E" available from KLA-TENCOR), whereby a residual film thickness was determined. The solubility in a TMAH developer solution was evaluated to be: "A" (favorable) in the case of the residual film thickness being less than 1 nm; "B" (unfavorable) in the case of the residual film thickness being no less than 1 nm; and "A'" in the case of dissolution of only the silicon-containing film being found through evaluation by means of a cross sectional SEM.

TABLE 3

| | Solvent resistance | Solubility in TMAH developer solution |
|---|---|---|
| Example 3 | A | A |
| Example 4 | A | A |
| Example 5 | A | A |
| Example 6 | A | A |

As demonstrated by the results shown in Table 3, according to the pattern-forming method of the embodiment of the present invention, the resist underlayer film can be dissolved by the use of the basic aqueous solution containing the TMAH developer solution as a component, without the application of dry removal or the use of concentrated aqueous hydrogen fluoride, and thereby the resist underlayer film and the silicon-containing film can be removed together.

According to the pattern-forming method of the embodiment of the present invention, the resist underlayer film and the silicon-containing film can be removed by dissolving the resist underlayer film without causing a severe damage to the substrate and reprocessing of the substrate is enabled. In addition, the resist underlayer film and the like can be conveniently removed without utilizing an ashing treatment and the like after the formation of the pattern of the substrate, and an influence etc. of the ashing treatment and the like on the substrate can be minimized. Therefore, the pattern-forming method can be suitably used for manufacture of semiconductor devices in which further progress of miniaturization is expected in the future.

Obviously, numerous modifications and variations of the present invention are possible in light of the above teachings. It is therefore to be understood that within the scope of the appended claims, the invention may be practiced otherwise than as specifically described herein.

The invention claimed is:

1. A pattern-forming method comprising:
forming a resist underlayer film on an upper face side of a substrate;
forming a silicon-containing film on an upper face side of the resist underlayer film;
forming a resist pattern on an upper face side of the silicon-containing film;
etching the silicon-containing film using the resist pattern as a mask; and
removing at least a part of the resist underlayer film and at least a part of the silicon-containing film with a basic aqueous solution.

2. The pattern-forming method according to claim 1, wherein the basic aqueous solution is a liquid comprising tetraalkylammonium hydroxide and water, or a liquid obtained by mixing ammonia, hydrogen peroxide and water.

3. The pattern-forming method according to claim 1, wherein the basic aqueous solution comprises none of hydrogen fluoride, a salt thereof, and a salt of a fluorine compound.

4. The pattern-forming method according to claim 1, wherein the removing of the resist underlayer film and the silicon-containing film is carried out at a temperature of less than 100° C.

5. The pattern-forming method according to claim 1, wherein the resist underlayer film is formed from a composition that comprises an aromatic ring-containing resin.

6. The pattern-forming method according to claim 5, wherein the aromatic ring-containing resin is a novolak resin, an acenaphthylene resin or a combination thereof.

7. The pattern-forming method according to claim 6, wherein the resin comprises a resin comprising a structural unit represented by formula (1):

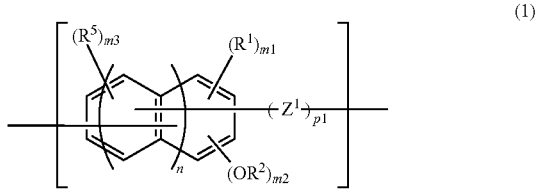

(1)

wherein, in the formula (1),
$Z^1$ represents a substituted or unsubstituted alkanediyl group, a substituted or unsubstituted arenediyl group or a substituted or unsubstituted oxyalkanediyl group;
p1 represents number of $Z^1$ that bonds to the aromatic ring, and is an integer of 1 to 10, wherein p1 is no less than 2, a plurality of $Z^1$s are identical or different;
$R^1$ and $R^5$ each independently represent a monovalent organic group having 1 to 20 carbon atoms;
m1 is an integer of 0 to 6, wherein in a case where m1 is no less than 2, a plurality of $R^1$s are identical or different;
m3 is an integer of 0 to 6, wherein in a case where m3 is no less than 2, a plurality of $R^5$s are identical or different;

$R^2$ represents a hydrogen atom or a monovalent organic group having 1 to 20 carbon atoms;
m2 is an integer of 1 to 8, wherein in a case where m2 is no less than 2, a plurality of $R^2$s are identical or different; and
n is an integer of 0 to 2,
wherein a sum of m1, m2, m3 and p1 is no greater than 10.

8. The pattern-forming method according to claim 7, wherein $R^2$ in the formula (1) represents —$R^3$—COOR$^4$, wherein $R^3$ represents a divalent organic group having 1 to 20 carbon atoms, and $R^4$ represents an organic group having 1 to 20 carbon atoms.

9. The pattern-forming method according to claim 8, wherein $R^3$ represents a group obtained by removing one hydrogen atom from at least one group selected from the group consisting of an alkyl group having 2 to 6 carbon atoms, an alkoxy group having 1 to 6 carbon atoms, an alkoxycarbonyl group having 2 to 10 carbon atoms, an aryl group having 6 to 14 carbon atoms, a glycidyl ether group, and an alkylglycidyl ether group, wherein the number of carbon atoms of the alkyl moiety of the alkylglycidyl group is 1 to 6.

10. The pattern-forming method according to claim 9, wherein $R^4$ represents a tertiary alkyl group.

11. The pattern-forming method according to claim 8, wherein $R^3$ represents a group obtained by removing one hydrogen atom from at least one group selected from the group consisting of an alkoxy group having 1 to 6 carbon atoms, an alkoxycarbonyl group having 2 to 10 carbon atoms, an aryl group having 6 to 14 carbon atoms, a glycidyl ether group, and an alkylglycidyl ether group, wherein the number of carbon atoms of the alkyl moiety of the alkylglycidyl group is 1 to 6.

12. The pattern-forming method according to claim 11, wherein $R^4$ represents a tertiary alkyl group.

13. The pattern-forming method according to claim 8, wherein $R^4$ represents a tertiary alkyl group.

14. The pattern-forming method according to claim 1, wherein the resist underlayer film is formed from a composition that comprises a calixarene compound.

15. The pattern-forming method according to claim 14, wherein the calixarene compound is represented by formula (2):

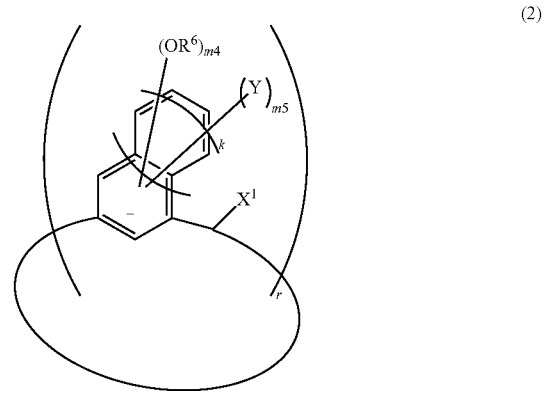

(2)

wherein, in the formula (2),
$R^6$ represents a hydrogen atom or a monovalent organic group having 1 to 30 carbon atoms;
r is an integer of 4 to 12;

Y represents a hydrocarbon group having 1 to 10 carbon atoms;
k is 0 or 1;
m4 is an integer of 1 to 3;
m5 is an integer of 0 to 7, wherein a sum of m4 and m5 is no greater than 8; and
$X^1$ represents a substituted or unsubstituted monovalent hydrocarbon group having 1 to 30 carbon atoms or a hydrogen atom,
wherein
in a case where m4 is no less than 2, a plurality of $R^6$s are identical or different,
in a case where m5 is no less than 2, a plurality of Ys are identical or different, and
in a case where r is no less than 2, a plurality of $X^1$s are identical or different, a plurality of ks are identical or different, a plurality of m4s are identical or different and a plurality of m5s are identical or different.

16. The pattern-forming method according to claim 1, wherein the silicon-containing film is formed from a composition comprising:
a hydrolytic condensation product of a silane compound comprising a compound represented by formula (3); and
an organic solvent,

wherein, in the formula (3),
$R^7$ represents a hydrogen atom, a fluorine atom, an alkyl group having 1 to 5 carbon atoms, a cyano group, a cyanoalkyl group, an alkylcarbonyloxy group, an acid anhydride group, an alkenyl group, an aryl group or an aralkyl group, wherein the alkyl group is unsubstituted or substituted with a fluorine atom, and the aryl group and the aralkyl group are unsubstituted or substituted;
$X^2$ represents a halogen atom or $-OR^8$, wherein $R^8$ represents a monovalent organic group; and
a is an integer of 0 to 3, wherein
in a case where $R^7$ is present in a plurality of number, a plurality of $R^7$s are identical or different, and
in a case where $X^2$ is present in a plurality of number, a plurality of $X^2$s are identical or different.

17. A resin comprising a structural unit represented by formula (1-1):

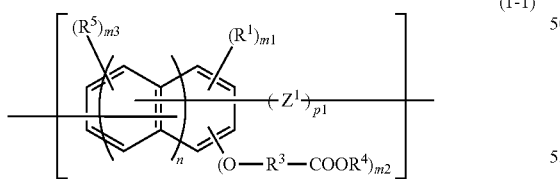

wherein, in the formula (1-1),
$Z^1$ represents a substituted or unsubstituted alkanediyl group, a substituted or unsubstituted arenediyl group or a substituted or unsubstituted oxyalkanediyl group;
p1 represents number of $Z^1$ that bonds to the aromatic ring, and is an integer of 1 to 10, wherein in a case where p1 is no less than 2, a plurality of $Z^1$s are identical or different;
$R^1$ and $R^5$ each independently represent a monovalent organic group having 1 to 20 carbon atoms;
m1 is an integer of 0 to 6, wherein in a case where m1 is no less than 2, a plurality of $R^1$s are identical or different;
m3 is an integer of 0 to 6, wherein in a case where m3 is no less than 2, a plurality of $R^5$s are identical or different;
m2 is an integer of 1 to 8;
$R^3$ represents a group obtained by removing one hydrogen atom from at least one group selected from the group consisting of an alkyl group having 2 to 6 carbon atoms, an alkoxy group having 1 to 6 carbon atoms, an alkoxycarbonyl group having 2 to 10 carbon atoms, an aryl group having 6 to 14 carbon atoms, a glycidyl ether group, and an alkylglycidyl ether group, wherein the number of carbon atoms of the alkyl moiety of the alkylglycidyl group is 1 to 6;
$R^4$ represents a tertiary alkyl group,
wherein in a case where m2 is no less than 2, a plurality of $R^3$s are identical or different and a plurality of $R^4$s are identical or different; and
n is an integer of 0 to 2,
wherein a sum of m1, m2, m3 and p1 is no greater than 10.

18. The resin according to claim 17, wherein $R^3$ represents a group obtained by removing one hydrogen atom from at least one group selected from the group consisting of an alkoxy group having 1 to 6 carbon atoms, an alkoxycarbonyl group having 2 to 10 carbon atoms, an aryl group having 6 to 14 carbon atoms, a glycidyl ether group, and an alkylglycidyl ether group, wherein the number of carbon atoms of the alkyl moiety of the alkylglycidyl group is 1 to 6.

19. A composition comprising a solvent and a resin which comprises a structural unit represented by formula (1-1):

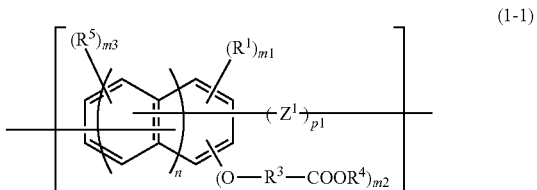

wherein, in the formula (1-1),
$Z^1$ represents a substituted or unsubstituted alkanediyl group, a substituted or unsubstituted arenediyl group or a substituted or unsubstituted oxyalkanediyl group;
p1 represents number of $Z^1$ that bonds to the aromatic ring, and is an integer of 1 to 10, wherein in a case where p1 is no less than 2, a plurality of $Z^1$s are identical or different;
$R^1$ and $R^5$ each independently represent a monovalent organic group having 1 to 20 carbon atoms;
m1 is an integer of 0 to 6, wherein in a case where m1 is no less than 2, a plurality of $R^1$s are identical or different;
m3 is an integer of 0 to 6, wherein in a case where m3 is no less than 2, a plurality of $R^5$s are identical or different;
m2 is an integer of 1 to 8;
$R^3$ represents a group obtained by removing one hydrogen atom from at least one group selected from the group consisting of an alkyl group having 2 to 6 carbon atoms, an alkoxy group having 1 to 6 carbon atoms, an alkoxycarbonyl group having 2 to 10 carbon atoms, an aryl group having 6 to 14 carbon atoms, a glycidyl ether group, and an alkylglycidyl ether group, wherein the number of carbon atoms of the alkyl moiety of the alkylglycidyl group is 1 to 6;

$R^4$ represents a tertiary alkyl group,
wherein in a case where m2 is no less than 2, a plurality of $R^3$s are identical or different and a plurality of $R^4$s are identical or different; and n is an integer of 0 to 2, wherein a sum of m1, m2, m3 and p1 is no greater than 10.

20. The composition according to claim 19, wherein $R^3$ represents a group obtained by removing one hydrogen atom from at least one group selected from the group consisting of an alkoxy group having 1 to 6 carbon atoms, an alkoxycarbonyl group having 2 to 10 carbon atoms, an aryl group having 6 to 14 carbon atoms, a glycidyl ether group, and an alkylglycidyl ether group, wherein the number of carbon atoms of the alkyl moiety of the alkylglycidyl group is 1 to 6.

* * * * *